(12) United States Patent
McAllen et al.

(10) Patent No.: US 7,788,369 B2
(45) Date of Patent: Aug. 31, 2010

(54) SYSTEM AND METHOD FOR NETWORK DISCOVERY AND CONNECTION MANAGEMENT

(75) Inventors: Christopher M. McAllen, Nashville, TN (US); Christopher W. Dern, San Diego, CA (US); Gregory A. Borges, San Diego, CA (US); Michael Scott Reed, San Diego, CA (US); Richard M. Batch, Del Mar, CA (US)

(73) Assignee: Carefusion 303, Inc., San Diego, CA (US)

( * ) Notice: Subject to any disclaimer, the term of this patent is extended or adjusted under 35 U.S.C. 154(b) by 1587 days.

(21) Appl. No.: 11/001,544

(22) Filed: Dec. 1, 2004

(65) Prior Publication Data

US 2005/0138428 A1    Jun. 23, 2005

Related U.S. Application Data

(60) Provisional application No. 60/526,182, filed on Dec. 1, 2003.

(51) Int. Cl.
    *G06F 15/173* (2006.01)
(52) U.S. Cl. .................... 709/224; 709/223; 726/2; 726/3; 726/4
(58) Field of Classification Search .......... 380/270; 370/329, 443
    See application file for complete search history.

(56) References Cited

U.S. PATENT DOCUMENTS

| | | | | |
|---|---|---|---|---|
| 6,052,727 | A * | 4/2000 | Kamalanathan | 709/224 |
| 6,252,884 | B1 * | 6/2001 | Hunter | 370/443 |
| 6,671,729 | B1 * | 12/2003 | Gordon et al. | 709/227 |
| 6,839,753 | B2 * | 1/2005 | Biondi et al. | 709/224 |
| 6,950,666 | B2 * | 9/2005 | Asakawa | 455/503 |
| 7,076,520 | B2 * | 7/2006 | Nelson et al. | 709/203 |
| 7,080,030 | B2 * | 7/2006 | Eglen et al. | 705/26 |
| 7,320,027 | B1 * | 1/2008 | Chang et al. | 709/219 |
| 7,328,210 | B2 * | 2/2008 | Barchi et al. | 707/6 |
| 7,349,630 | B2 * | 3/2008 | Melaragni | 398/75 |
| 7,382,741 | B2 * | 6/2008 | Rao | 370/255 |
| 7,401,118 | B1 * | 7/2008 | Yokota et al. | 709/203 |
| 7,614,081 | B2 * | 11/2009 | Prohel et al. | 726/18 |
| 2002/0023143 | A1 * | 2/2002 | Stephenson et al. | 709/218 |
| 2002/0052885 | A1 * | 5/2002 | Levy | 707/200 |
| 2002/0062366 | A1 | 5/2002 | Roy et al. | |
| 2002/0078461 | A1 * | 6/2002 | Boykin | 725/87 |
| 2002/0120676 | A1 * | 8/2002 | Biondi et al. | 709/203 |
| 2003/0206116 | A1 | 11/2003 | Weiner et al. | |
| 2004/0133669 | A1 * | 7/2004 | Jalonen et al. | 709/224 |

OTHER PUBLICATIONS

"Universal Plug and Play Device Architecture," UPnP, Version 1.0, Internet, Jun. 8, 2000, 1999-2000 Microsoft Corporation.
PCT "International Search Report," Feb. 24, 2005, pp. 1-4.

* cited by examiner

*Primary Examiner*—Ponnoreay Pich
(74) *Attorney, Agent, or Firm*—McDermott Will & Emery LLP

(57) ABSTRACT

The present invention provides for a system and method of discovering whether a medical device is connected to a network, establishing secure communications between and a server and the medical device, and communicating with the medical device. Also disclosed is a method of encryption to ensure secure communications within the network between a server and medical devices connected to the network. The invention also includes a system and method for determining the location of medical devices within an institution.

7 Claims, 8 Drawing Sheets

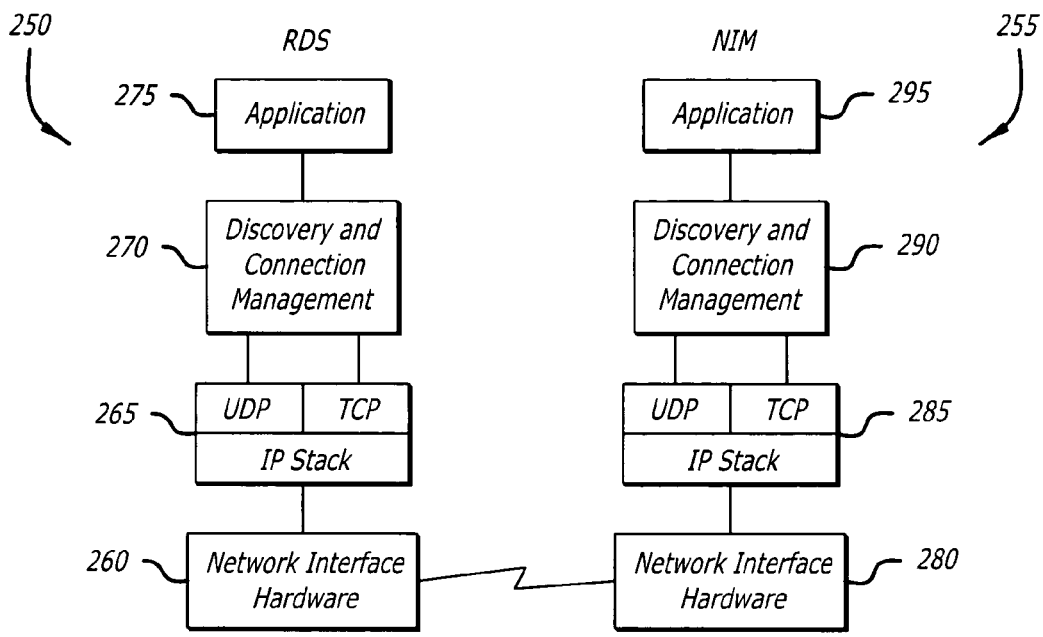

FIG. 4

| message ID (0x00=RDS Beacon) | registration mod | registration key | closed endpoint list start offset |
|---|---|---|---|
| closed endpoint list entry count | closed endpoint list entry lifetime | beacon interval (in milliseconds) | |
| UTC time of year (in milliseconds) | | | |
| UTC year | | local time offset (in +/- minutes) | |
| possible addition data (future revisions) | | | |
| list of closed endpoint IP address (32 bits per entry) | | | |
| list of closed endpoint port numbers (16 bits per entry) | | | |

FIG. 5

| 0 | 7 | 8 | 15 | 16 | 23 | 24 | 31 |
|---|---|---|---|---|---|---|---|
| message ID (0x80=NIM Status) || endpoint list start offset || connected endpoint count || listening endpoint count ||
| possible addition data (future revisions) ||||||||
| list of connected endpoint port numbers (16 bits per entry) ||||||||
| list of listening endpoint port numbers (16 bits per entry) ||||||||

# SYSTEM AND METHOD FOR NETWORK DISCOVERY AND CONNECTION MANAGEMENT

CROSS-REFERENCES TO RELATED APPLICATIONS

This application claims the benefit of priority to U.S. Provisional Application No. 60/526,182, filed Dec. 1, 2003, the subject matter of which is being incorporated herein in its entirety.

BACKGROUND OF THE INVENTION

1. Field of the Invention

The present invention is generally directed to a system and method used on a server-client network by a server to discover clients that are connected to the network and to open communications sessions with the discovered client. More specifically, the present invention is directed to a server-client system operating on a network wherein the server broadcasts a beacon to the entire network through a particular port. Clients connected to the system listen on the particular port for the beacon, and if the beacon is detected, responds through the port with information that may then be used by the server to open a secure communication session with the client.

2. General Background and State of the Art

The delivery of therapy and the collection of patient data from bedside equipment, laboratory equipment and institutional information systems has become more integrated with the advent of more capable and reliable computer networks, faster and larger storage media, and the miniaturization of computer processors and memory. This technology has resulted in the inclusion of computer processors or microprocessors and memory in a wide variety of medical equipment. Inclusion of communications capability allows the processors and memory in the medical equipment to be tied into ward, department and institution wide networks. These networks allow for the exchange of information between various institutional information systems and individual medical devices. The devices may be therapy delivery devices, such as infusion pumps, or they may be vital signs measurement and data collection devices, including both bedside monitors and laboratory equipment.

As the complexity of therapeutic medication delivery has increased, one problem that has arisen is that there are more opportunities for error. Many different systems have been proposed to address the frequency of the medication error, such as the system described in U.S. Pat. No. 5,781,442, entitled "System and Method for collecting Data and Managing Patient Care" issued to Engleson et al., the subject matter of which is intended to be, and is, incorporated into and is a part of the subject matter of this provisional patent application. Another system is described in U.S. Patent Publication No. 2002/0169636 entitled "System and Method for Managing Patient Care" by Eggers, the subject matter of which is intended to be, and is, incorporated into and is a part of the subject matter of this provisional patent application.

One problem that occurs with systems having many client medical devices is that it is necessary to ensure that the memory of the various devices on the system are updated frequently enough so that the devices have access to up-to-date patient information, therapeutic information, rule sets and patient specific medication guidelines. Until recently, it has been necessary for servers to poll each device connected to a network to determine if the device was connected to the network, and to then send the device any updated information. Such polling is resource and time intensive, and may decrease the efficiency and speed of the entire network.

This problem is particularly difficult where the medical devices utilize a media other than a hard wired network, such as a wireless network, or the internet. In these systems, individual medical devices may call the server through an access point of the wireless network, or over the internet, using either a dial-up, cable, DSL or wireless connection. In such systems, there is a potential security problem in that the networks are essentially wide open to requests for communication that come from an external source. The system must determine whether the communication request is coming from a secure medical device, or some un-secure source which should be prevented from establishing communication with the server.

What has been needed, and heretofore unavailable, is a system and method for discovering whether a client medical device is connected to the network and establishing a secure communication session through the network between the server and the medical device. Such a system should be reliable, robust and insure that communication sessions between server and client are secure.

SUMMARY OF THE INVENTION

The present invention is generally embodied in a system having one or more servers and one or more clients that are connected to a network. The present invention generally provides a method for discovering what clients are connected to the network, for registering the client with the server, and for providing secure communications between the server and the client. A communication session established between a server and client in accordance with the methods of the present invention is particularly robust in that it inherently provides for re-establishing connections that are dropped for whatever reason, and rejects attempts by rogue or third party servers to connect to the network.

In one aspect, the present invention includes a remote data server and one or more clients connected to a network. The clients are connected to the network through a network interface module. The server periodically transmits beacon messages over the network. The client listens to the network, and if the client receives the beacon message, replies to the beacon message with a status reply message, thus registering the client with the server and allowing the server to establish a secure communication session. Each message includes specific fields of information. In one embodiment, the beacon message is transmitted from a specific port, and the client is programmed to receive beacon messages only from that port, and to respond to that port. In another embodiment, the beacon and status reply messages are transmitted over a UDP port. In still another embodiment, once the server has received a status reply message, the server opens a TCP/IP connection with the client.

In yet another aspect, the client is programmed to ignore any beacon message that comes from a server that the client is not registered with. In one embodiment, the client ignores beacon messages that are not separated by a specified interval. In another embodiment, the client is programmed to ignore any beacon messages transmitted by a second server, unless a specified interval has elapsed since the client received a beacon message from the server is was previously registered with.

In another aspect, the present invention includes a method for encrypting messages transmitted over the network to protect the privacy of patient and other data. In one embodiment, messages are encrypted using security headers and footers, with the entire message being encrypted using the AES block cipher after salting the message by XORing the entire message with a transaction key.

In still another aspect of the present invention, the connections between servers and clients on the network are managed by creation by the server of TCP/IP connections to each endpoint of each client. Only the server is allowed to establish a TCP/IP connection to a client, thus ensuring that the client does not respond to any server it is not registered with.

In yet a further aspect, the present invention provides a method for determining the location of a mobile client within an institution. It will be understood that the mobile client may be a processor included within a medical device. In one embodiment where the client is connected to the network using a wireless connection, the identification of the MAC address to which the client is connected is known and can be associated with a location within the institution. In another embodiment, a watch list of clients which have not registered with the server for a predetermined period of time, thus assumed to be "lost," may be produced. When one of the clients on the watch list is powered up, or comes into range of a wireless transmitter/receiver, a report of the approximate location of the device as determined from the MAC address is provided.

In still another aspect, the present invention includes a system and method wherein a client, such as a medical device, may be powered down, or placed in a suspense, standby or sleep mode, and the client may be programmed to "wake up" at specified intervals to register with the server and determine if any updates to databases associated with the client are available, and if so, to download the updates. Once the download is complete, the client is programmed to wait a specified interval for further updates, and then return to standby sleep mode. Alternatively, the client may return to standby or sleep mode upon completion of the download. In another arrangement, a network interface module associated with the client may be programmed to wake up, while the client itself remains in the standby mode.

Other features and advantages of the invention will become apparent from the following detailed description, taken in conjunction with the accompanying drawings, which illustrate, by way of example, the features of the invention.

BRIEF DESCRIPTION OF THE DRAWINGS

FIG. 4 is a graphical illustration of the software stacks of an RDS server and a NIM client showing the layers of the software architecture, including the discovery and connection management layer of the present invention.

FIG. 5 is a diagram illustrating the data structure of a beacon message transmitted by a RDS in accordance with one embodiment of the present invention.

DETAILED DESCRIPTION OF THE PREFERRED EMBODIMENTS

Figure 1:
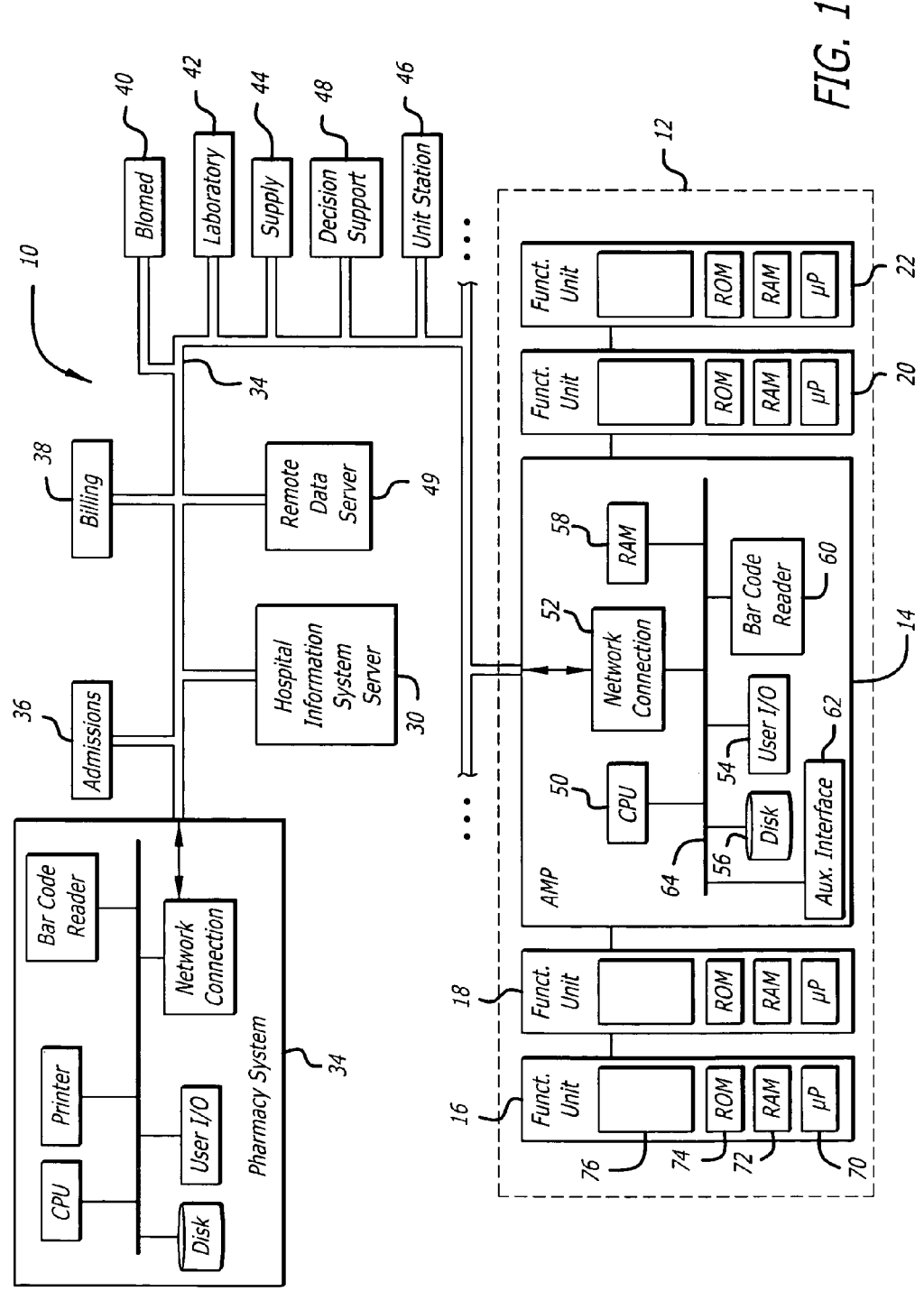
FIG. 1 is a graphical illustration of a patient care system utilizing various aspects of the present invention.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

As will be appreciated by one of skill in the art, the present invention may be embodied as a method, data processing system, or computer program product. Accordingly, various aspects of the present invention may take the form of a hardware embodiment, a software embodiment, or an embodiment combining software and hardware. Furthermore, the present invention may take the form of a computer program product on a computer-usable storage medium having computer readable program code means embodied in the medium. Any suitable computer readable medium may be utilized including, but not limited to, hard disks, CD-ROMs, optical storage devices, and magnetic storage devices and the like.

The present invention is described below with reference to flowchart illustrations of methods, apparatus (systems), and computer program products according to an embodiment of the invention. It will be understood that each block of the flowchart illustrations, and combinations of blocks in the flowchart illustrations, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

The present invention can be implemented as a system running on a stand alone computing device. Preferably, the present invention is implemented as a system in a client-server environment. As is known to those of skill in the art, a client application is the requesting program in a client-server relationship. A server application is a program that awaits and fulfills requests from client programs in the same or other computers. Client-server environments may include public networks, such as the Internet, and private networks often referred to as "intranets", local area networks (LANs) and wide area networks (WANs), virtual private networks (VPNs), frame relay or direct telephone connections. It is understood that a client application or server application, including computers hosting client and server applications, or other apparatus configured to execute program code embodied within computer usable media, operates as means for performing the various functions and carries out the methods of the various operations of the present invention.

The following terms and definitions are useful in fully understanding the various aspects and embodiments of the present invention. Accordingly, these terms are intended, for the purposes of describing the present invention, to have the meanings set forth as follows:

AES means Advanced Encryption Standard. AES is a next-generation replacement for the Defense Encryption Standard (DES), and is a highly-secure symmetric block encryption algorithm approved by the Federal Information Processing Standard and the National Institute of Standards and Technology.

CBC means Cipher Block Chaining. CBC is a mode of operation for block ciphers where each block of plaintext is XORed with the previously encoded block of ciphertext, before it is encoded.

DHCP means Dynamic Host Configuration Protocol. DHCP provides for dynamically assigning IP addresses to clients on an IP network.

ECB means Electronic Cook Book. ECB is a mode of operation for blocking ciphers where each block of plaintext is encoded independently of all other blocks.

IP means Internet Protocol. IP is a simple addressing protocol used to deliver network messages. Many versions of IP exists, and the various embodiments of the present invention are intended to operate using any version of IP, and preferably version 4 (IPv4).

LAN means Local Access Network. A LAN is a group of systems connected over a private, homogenous network.

MD5 stands for the MD5 Message Digest Algorithm. MD5 is a complex hashing algorithm designed to produce a secure and unique "fingerprint" of a given data set.

NIM means network interface module, and is a device that allows medical devices to connect to and participate on an IP network.

RDS stands for Remote Data Server, typically a central server that serves as a proxy for all third party communication with networked medical devices.

TCP means Transmission Control Protocol. TCP is a high level protocol that provides a persistent, reliable stream-based data connection between two clients on a network.

UDP stands for User Datagram Protocol. UDP is a low-level protocol that provides relatively unreliable message-based communications between clients on a network.

FIG. 1 is a general illustration of a patient care system utilizing aspects of the present invention. In FIG. 1, a patient care device 12 is connected to a hospital network 10 including a pharmacy management system 34 and a hospital information system server 30. Each element 12, 30 and 34 is connected to network 10 by a transmission channel 32. Transmission channel 32 is any wired or wireless transmission channel, for example a 802.11 wireless local area network (LAN). In an embodiment of the present invention, network 10 also includes computer systems located in various departments throughout a hospital. For example, network 10 of FIG. 1 optionally includes computer systems associated with an admissions department 36, a billing department 38, a biomedical engineering department 40, a clinical laboratory 42, a central supply department 44, one or more unit station computers and/or a medical decision support system 48. Additionally, the system may incorporate a separate remote data server 49, the function of which will be described in more detail below. Moreover, although the remote data server 49 is shown as a separate server, the functions and programming of the remote data server 49 may be incorporated into another computer, such as, for example, the hospital information system server 30, if such is desired by engineers designing the institution's information system.

Patient care device 12 preferably comprises a system similar to that described in U.S. Pat. No. 5,713,856 to Eggers et al., which is incorporated herein by reference. Alternatively, other patient care devices, such as pumps, physiological monitors (e.g., heart rate, blood pressure, ECG, EEG, pulse oximeter, and other patient monitors), therapy devices, and other drug delivery devices may be utilized according to the teachings set forth herein. Patient care device 12 preferably comprises a control module 14, also referred to as interface unit 14, connected to one or more functional modules 16, 18, 20, 22. Interface unit 14 includes a central processing unit (CPU) 50 connected to a memory, for example, random access memory (RAM) 58, and one or more interface devices such as user interface device 54, a coded data input device 60, a network connection 52, and an auxiliary interface 62 for communicating with additional modules or devices. Interface unit 14 also preferably, although not necessarily, includes a main non-volatile storage unit 56, preferably a hard disk drive, for storing software and data and one or more internal buses 64 for interconnecting the aforementioned elements.

In a typical embodiment, user interface device 54 is a touch screen for displaying information to a user and allowing a user to input information by touching defined areas of the screen. Alternatively, user interface device 54 could include any means for displaying and inputting information, such as a monitor, a printer, a keyboard, softkeys, a mouse, a track ball and/or a light pen. Coded data input device 60 is preferably a bar code reader capable of scanning and interpreting data printed in bar coded format. Alternatively, data input device 60 could be any device for entering coded data into a computer, such as devices for reading a magnetic strips, PCMCIA smart cards, radio frequency cards, memory sticks, CDs, DVDs, or any other analog or digital storage media. Other examples of data input device 60 include a voice activation or recognition device or a portable personal data assistant (PDA). Depending upon the types of interface devices used, user interface device 54 and coded data input device 60 may be the same device. Alternatively, although data input device 60 is shown in FIG. 1 to be disposed within interface unit 14, one skilled in the art will recognize that data input device 60 may be integral within pharmacy system 34 or located externally and communicating with pharmacy system 34 through an RS-232 serial interface or any other appropriate communication means. Auxiliary interface 62 is preferably an RS-232 communications interface, however any other means for communicating with a peripheral device such as a printer, patient monitor, infusion pump or other medical device may be used without departing from the scope of the invention. Additionally, data input device 60 may be a separate functional module, such as modules 16, 18, 20 and 22, and configured to communicate with controller 14, or any other system on the network, using suitable programming and communication protocols.

Network connection 52 is preferably a direct network connection such as a T1 connection, an integrated services digital network (ISDN) connection, a digital subscriber line (DSL) modem or a cable modem. Alternatively, any direct or indirect network connection may be used, including, but not limited to a telephone modem, an MIB system, an RS232 interface, an auxiliary interface, an optical link, an infrared link, a radio frequency link, a microwave link or a WLANS connection or other wireless connection.

Functional modules 16, 18, 20, 22 are any devices for providing care to a patient or for monitoring patient condition. As shown in FIG. 1, at least one of functional modules 16, 18, 20, 22 may be an infusion pump module such as an intravenous infusion pump for delivering medication or other fluid to a patient. For the purposes of this discussion, functional module 16 is an infusion pump module. Each of functional modules 18, 20, 22 may be any patient treatment or monitoring device including, but not limited to, an infusion pump, a syringe pump, a PCA pump, an epidural pump, an enteral pump, a blood pressure monitor, a pulse oximeter, an EKG monitor, an EEG monitor, a heart rate monitor or an intracranial pressure monitor or the like. Alternatively, functional module 18, 20 and/or 22 may be a printer, scanner, bar code reader or any other peripheral input, output or input/output device.

Each functional module 16, 18, 20, 22 communicates directly or indirectly with interface unit 14, with interface unit 14 providing overall monitoring and control of device 12. Functional modules 16, 18, 20, 22 are connected physically and electronically in serial fashion to one or both ends of interface unit 14 as shown in FIG. 1 and as detailed in Eggers et al. However, one skilled in the art will recognize that there are other means for connecting functional modules with the interface unit that may be utilized without departing from the scope of the invention. It will also be appreciated that devices such as pumps or patient monitoring devices that provide sufficient programmability and connectivity may be capable of operating as stand-alone devices and may communicate directly with the network without connected through a separate interface unit or control unit 14. As described above, additional medical devices or peripheral devices may be connected to patient care device 12 through one or more auxiliary interfaces 62.

Each functional module 16, 18, 20, 22 typically includes module-specific components 76, a microprocessor 70, a volatile memory 72 and a nonvolatile memory 74 for storing information. It should be noted that while four functional modules are shown in FIG. 1, any number of devices may be connected directly or indirectly to central controller 14. The number and type of functional modules described herein are intended to be illustrative, and in no way limit the scope of the present invention. Module-specific components 76 include any components necessary for operation of a particular module, such as a pumping mechanism for infusion pump module 16.

While each functional module is typically capable of a least some level of independent operation, interface unit 14 monitors and controls overall operation of device 12. For example, as will be described in more detail below, interface unit 14 provides programming instructions to the functional modules 16, 18, 20, 22 and monitors the status of each module.

Patient care device 12 is capable of operating in several different modes, or personalities, with each personality defined by a configuration database. A particular configuration database is selected based, at least in part, by patient-specific information such as patient location, age, physical characteristics, or medical characteristics. Medical characteristics include, but are not limited to, patient diagnosis, treatment prescription, medical history, medical records, patient care provider identification, physiological characteristics or psychological characteristics. As used herein, patient-specific information also includes care provider information (e.g., physician identification) or a patient care device's 10 location in the hospital or hospital computer network. Patient care information may be entered through interface device 52, 54, 60 or 62, and may originate from anywhere in network 10, such as, for example, from pharmacy 34, admissions 36, laboratory 42, and the like.

Data to and from the various data sources can be converted into network-compatible data with existing technology, and movement of the information between the medical device and network can be accomplished by a variety of means. For example, patient care device 12 and network 10 may communicate via automated interaction, manual interaction or a combination of both automated and manual interaction. Automated interaction may be continuous or intermittent and may occur through direct network connection 54 (as shown in FIG. 1), or alternatively through RS232 links, MIB systems, RF links such as BLUETOOTH (Amtel Corp., San Jose, Calif.), IR links, WLANS, digital cable systems, telephone modems or other wired or wireless communication means. Manual interaction between patient care device 12 and network 10 involves physically transferring, intermittently or periodically, data between systems using, for example, user interface device 54, coded data input device 60, bar codes, computer disks, portable data assistants, memory cards, or any other media for storing data. Preferably, the communication means is bidirectional with access to data from as many points of the distributed data sources as possible. Decision-making can occur at a variety of places within network 10. For example, and not by way of limitation, decisions can be made in HIS server 30, decision support 48, remote data server 49, hospital department or unit stations 46, or within patient care device 12 itself.

A client-server environment incorporating aspects of the present invention typically includes a central server that is accessible by at least one client via a computer network. In more complex systems, the central server may be accessible by at least one local server via a computer network, such as, for example, an Ethernet, wireless network, or the Internet which may in turn be accessed by a client. A variety of computer network transport protocols including, but not limited to TCP/IP, can be utilized for communicating between the central server, any local servers, and client devices configured with a communications capability compatible with the communication protocol used on the network.

The central server generally includes a central database, such as the Microsoft® SQL Server application program, version 6.5 (available from Microsoft, Inc., Redmond, Wash.) or the like, executing thereon. The central server may ensure that the local servers are running the most recent version of a knowledge base, and also may store all patient data and perform various administrative functions including adding and deleting local servers and users to the system. The central server may also provides authorization before a local server or client medical device can be utilized by a user. As stated previously, in typical integrated systems, patient data is preferably stored on the central server, thereby providing a central repository of patient data. However, it is understood that patient data can be stored on a local server or on local storage media, or on another hospital or institutional server or information system, where it may be accessed through the various elements of the system, that is, by local servers or clients, as needed.

Each local server typically serves multiple users in a geographical location. Examples of such a local server include, servers located in hospital wards, at nurse stations or at off-site or remote locations operating either as primary or back-up information collection, routing, analysis and/or storage systems. Each local server typically includes a server application, one or more knowledge bases, and a local database. Each local server may also include an inference system capable of interacting with sets of rules or practice criteria for ensuring that proper medical and medication delivery and prescribing practices are followed. Each local server may also perform artificial intelligence processing for carrying out operations of the present invention. When a user logs on to a local server via a client, the user is preferably authenticated via an identification and password, as would be understood by those skilled in the art. Once authenticated, a user is permitted access to the system and certain administrative privileges are assigned to the user. Alternatively, the system may be programmed to operate such that various patient, care-giver and medication identification devices, such as bar coded labels, RF identification tags or devices, or other smart, passive or active identification devices may be used to identify users of the systems and allow access to the system for diagnosing and treating patients.

Each local server may also communicate with the central server to verify that the most up-to-date version of the knowledge base(s) and application(s) are running on the requesting local server. If not, the requesting local server downloads from the central server the latest validated knowledge base(s) and/or application(s) before a user session is established. While in some embodiments of the present invention most of the computationally intensive work, such as data and artificial intelligence processing, is performed on a local server, allowing "thin" clients that is, computing devices having minimal hardware and optimizing system speed, the present invention is also intended to include systems where data processing and rules processing is carried out on the clients, freeing the central system, or local server, from such tasks.

Each local client or medical device also includes a client application program that typically consists of a graphical user interface (GUI), although such is not necessary on many medical devices, and a middle layer program that communicates with central or local servers. Program code for the client application program may execute entirely on the local client, or it may execute partly on the local client and partly on the central or local server.

Computer program code for carrying out operations of the present invention is preferably written in an object oriented programming language such as, for example, JAVA®, Smalltalk, or C++. However, the computer program code for carrying out operations of the present invention may also be written in conventional procedural programming languages, such as the "C" programming language, in an interpreted scripting language, such as Perl, or in a functional (or fourth generation) programming language such as Lisp, SML, Forth, or the like. The software may also be written to be compatible with HLA-7 requirements.

Exemplary embodiments of the present invention will now be discussed. Typically, medical devices incorporating aspects of the present invention will be equipped with a Network Interface Module (NIM), allowing the medical device to participate as a node in a network. While for purposes of clarity the present invention will be described as operating in an Ethernet network environment using the Internet Protocol (IP), it will be understood by those skilled in the art that concepts of the present invention are equally applicable in other network environments, and such environments are intended to be within the scope of the present invention.

All direct communications with medical devices operating on a network in accordance with the present invention are performed through a central server, known as the remote data server (RDS). In accordance with aspects of the present invention, network interface modules incorporated into medical devices such as, for example, infusion pumps or vital signs measurement devices, ignore all network traffic that does not originate from an authenticated RDS. The primary responsibilities of the RDS of the present invention are to track the location and status of all networked medical devices that have NIMs, and maintain open communication channels with them.

In a typical embodiment of the present invention, the architecture of the software and communications protocols comprising the means by which the RDS discovers, connects to, and communicates with networked medical devices will operate, for example, in an Ethernet LAN environment. The nominal round-trip-time for data between any two nodes on the LAN will typically be less than 1 second and every link on the network is generally capable of transmitting data at a sustained rate of at least 1 Mb/sec. While a typical network will be considered to be running efficiently if no more than 10% of the total network bandwidth is available for use at any given time, it is understood that nodes may suffer from intermittent network connectivity, as would occur in a wireless network environment, and that such interruptions in connectivity may vary widely in both severity and duration.

Figure 2:
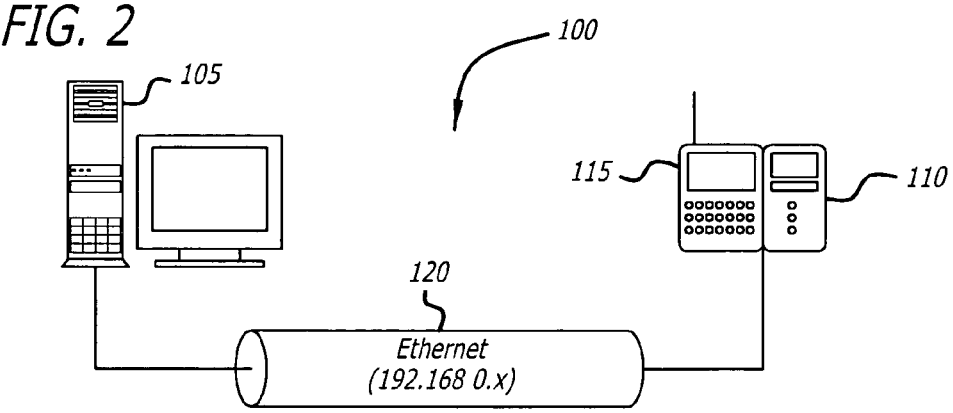
FIG. 2 is a graphical illustration of a simplified network illustrating the principles of the present invention.

FIG. 2 depicts the present invention in its simplest embodiment. In this embodiment, a system in accordance with principles of the present invention consists of a single remote data server 105 and a single medical device 110 attached to a network interface module 115 connected together via a suitable communication means, such as, for example, an Ethernet cable 120. While the connection between RDS 105 and NIM 115 is depicted by the ethernet cable 120, those skilled in the art will appreciate that any means, either wired or wireless, may be used to place RDS 105 and NIM 115 in communication with each other, providing for the flow of information between them.

Figure 3:
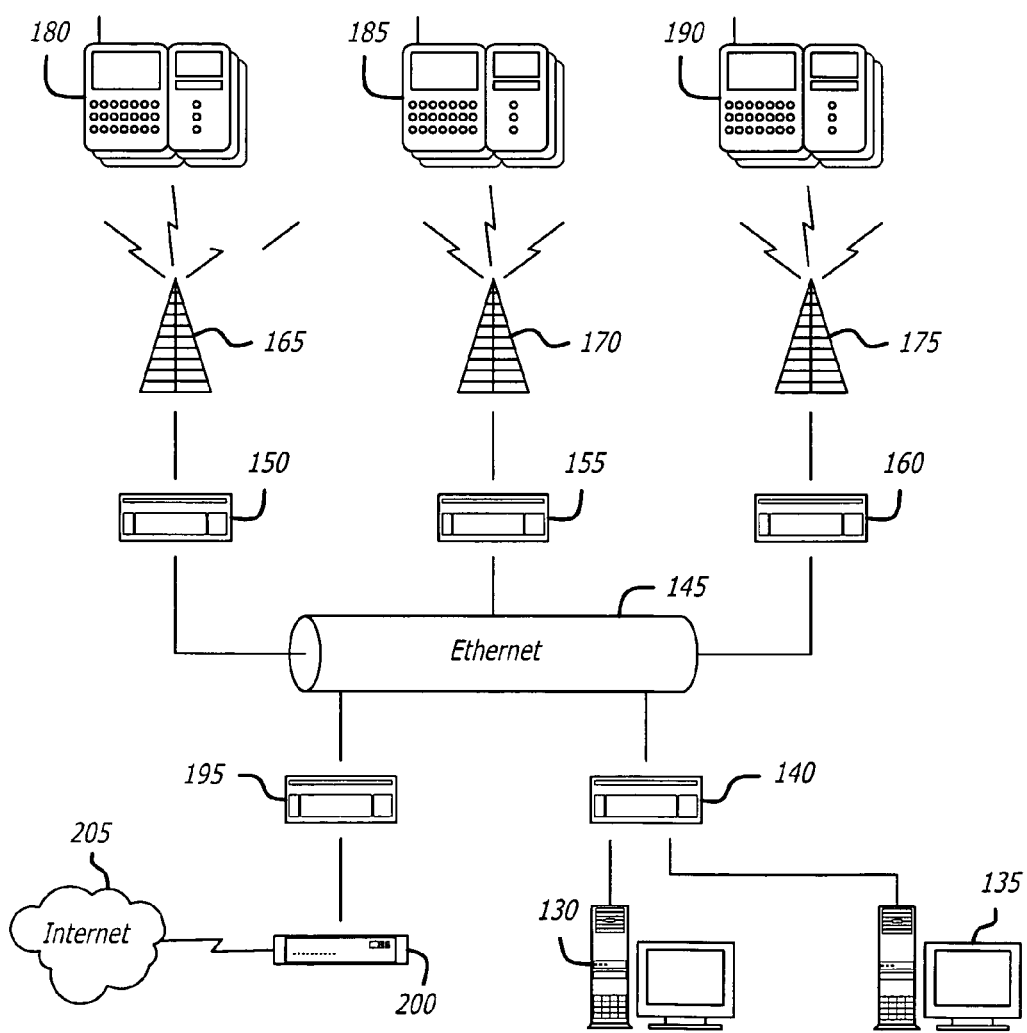
FIG. 3 is a graphical illustration of a complex network illustrating the principles of the present invention.

A more complex system operating in accordance with aspects of the present invention is depicted in FIG. 3. In this embodiment, the system comprises a primary RDS 130 and a backup RDS 135 connected through router 140 to an ethernet 145. Information communicated to and from RDSs 130, 135 through ethernet 145 is communicated through routers 150, 155 and 160 and transmitter/receiver wireless access points 165, 170 and 175 to medical devices 180, 185 and 190. As described above, medical devices 180, 185 and 190 include network interface modules which include suitable circuitry for wireless transmission and reception of the information to and from wireless access points 165, 170 and 175. It will be understood that the size and the complexity of the network is not limited by the depiction of FIG. 3. The size and/or complexity of the network is, however, independent of the protocol used for discovery and connectivity.

Additionally, information may flow into or out of the system through router 195 and firewall or internet proxy 200 to another system, such as an internet or intranet 205. In this manner third party systems or devices may communicate with the medical devices 180, 185, 190. As will be discussed in further detail below, the architecture and operation of the system of the present invention provides for the secure flow of information within the network. When third party devices (not shown) wish to communicate with a networked medical device 180, 185, 190, they do so by sending their requests through ethernet 145 to an active RDS, such as RDS 130 or 135. The RDS then makes the requests to the networked medical devices, if possible, on behalf of the third party devices. At no time do third party devices initiate direct communication with a networked medical device through its NIM. In this manner, security of the communication session is ensured in that no outside third party device is allowed to initiate a communication with the networked medical device. Any third party request that does not initiate through the RDS is ignored.

Addressing

In a preferred embodiment of the present invention, the connectivity protocol of the system operates over IP/Ethernet. In this embodiment, each NIM in the system is assigned a unique IP address in order for communication to be possible. IP addresses may be statically assigned, or a user may choose to use DHCP for dynamic address assignment. Both methods are supported by the NIM.

Redundant Servers

Since all communications to and from medical devices 180, 185 and 190 are routed through an RDS, the RDS is the most significant point of failure in the system. End users that desire enhanced fault tolerance may choose to set up one or more redundant RDS systems on their network, as exemplified in FIG. 3 by primary RDS 130 and backup RDS 135. Such redundancy is fully supported by the connectivity protocol of the present invention, and the redundant servers are typically set up in an active/passive configuration.

Backup remote data servers, such as RDS 135, in a redundant cluster may be connected directly to the network and assigned unique IP addresses, or they may be connected, as is known in the art, through a translating router (not shown) so they all appear to have the same IP address. The connectivity protocol of the operating system incorporating the present invention supports both configurations.

Load Balancing

In very large networks where multiple subnets exist, a redundant cluster can be used for load balancing by dividing up the subnets into logical groups, and assigning groups to individual remote data servers. The only limitation on such a system is that a single subnet can not be serviced by more than one RDS. To ensure the security of connections betweens RDSs and NIMS, a NIM will typically be programmed to refuse to reply to a RDS if it detects more than one active RDS on its local subnet.

As depicted in FIG. 3, the network, here an Ethernet, acts as a conduit for information between medical devices and a primary and back-up RDSs. The Ethernet may also allow for connection to the internet through a firewall and/or internet proxy. Typically, both the internet access and RDS server arrangement communicate with the Ethernet through a suitable router. As shown, a plurality of medical devices may also be connected to the Ethernet and thus be in communication with the RDS. As depicted in FIG. 3, the medical devices are in communication with the Ethernet through appropriate routers that provides signals to a wireless access point. The broadcast signals may be received by the medical devices, which in turn may transmit signals over the wireless access points that are then communicated over the Ethernet to a desired destination. Alternatively, the medical devices may be hardwired to the Ethernet, thus obviating the need for wireless access points. In still another alternative, the router and wireless access point may be combined into a single unit.

Software Architecture

FIG. 4 illustrates an exemplary embodiment of the software architecture of the present invention. As shown in FIG. 4, the software stacks on the RDS 250 and NIM 255 appear to be similar, although as will be discussed below, the software running in the application layers 260, 280 may be quite different, reflecting the different functions of the RDS 250 and NIM 255. The discovery and connection management protocol layer 275 of the RDS 250 and discovery and connection management protocol layer 290 of the NIM 255 fit into the software stacks on the RDS and NIM systems between the application levels 275, 295 and the connection levels 265, 290. On the NIM 255, the discovery and connection management layer 290 of the operating program is responsible for locating and registering a medical device associated with NIM 255 with a valid RDS 250. On the RDS 250, the discovery and connection management layer 270 is responsible for maintaining a list of all active NIMs 255. Both the RDS 250 and NIM 255 sides are responsible for maintaining TCP/IP connections between each other, and for transmitting and receiving data over those connections on behalf of their respective application layers 275, 295.

The layers 265, 260 of RDS 250 and 285, 280 of NIM 255 beneath the respective discovery and connection management layers 270, 290 represent a standard TCP/IP stack, as that term is understood by those skilled in the art, and are typically the same on both the RDS 250 and NIM 255. The application layers 275, 295 includes any high-level software program code that interfaces with the connection layers 270, 290.

Discovery

Before any communication can take place between the RDS 250 and devices attached to a NIM 255, the two systems must locate each other on the network and establish a connection. This process, for the purposes of this description, is known as discovery.

RDS Beacon

When an RDS 250 incorporating the system and method of the present invention is ready to begin communication with and servicing medical devices connected to NIMs 255, the RDS 250 begins transmitting a special "beacon" message across the network. The purpose of this beacon is to alert the NIMs 255 connected to various medical devices of the presence of the RDS 250 on the network. The beacon is transmitted via UDP broadcast over the network, which may be an ethernet or wireless network, to a well-known port on every subnet serviced by the RDS 250. NIMs 255 are programmed to listen for this beacon upon startup of the NIM 255 to discover the location of the RDS 250 with which they will communicate. Alternatively, NIMs 255 may be programmed to periodically look for the beacon signal or message. In this embodiment, such periodic listening for the beacon may be useful in re-establishing connection with the RDS 250 where the communication link has been lost for some reason.

In a presently preferred embodiment, a RDS beacon signal or message according to the present invention is typically broadcast at a fixed interval (typically one second) on the subnets it services. Generally, the RDS 250 broadcasts beacon messages indefinitely until the RDS 250 goes offline. The RDS 250 continues to broadcast beacon messages because, once connected, the NIMs 255 of each medical device connected to the network keep listening for the beacon (for various reasons) and may terminate their connections with the RDS 250 if a beacon is not received within a pre-determined period of time.

FIG. 5 depicts the data format of one embodiment of a RDS beacon message. The message consists of a number of fields having different data lengths, depending on the particular field. Preferably, all data fields greater than one byte in length are stored in little-endian format, and the total size of the beacon message of this embodiment never exceeds 512 bytes, although it is possible to construct a valid beacon message larger than this, and such messages are intended to be within the scope of the present invention. An additional layer of encryption may be applied to the beacon message before it is transmitted to further enhance security. Each of the fields of the beacon message are discussed in detail below.

Message ID

The first byte of the beacon message is the Message ID. This byte is constant, and is used to identify the message as a RDS beacon.

Registration Mod and Key

Certain types of global network interruptions (such as, for example, a router rebooting) can cause temporary interruption of communication in an active RDS/NIM network. The effect of such an interruption is that each affected NIM is likely to drop its connections with the RDS and attempt to re-register with the RDS. After such a disruption, the RDS could become overloaded with potentially several thousand simultaneous registration requests once connectivity is restored. Accordingly, the beacon message includes a throttling mechanism to reduce the load on the RDS in such a situation.

In one embodiment of the present invention, referring again to FIG. 5, when a NIM receives a valid beacon message from an RDS, the NIM computes the modulo of its IP address using the data contained in the registration mod field of the beacon message. If the result is equal to a value stored in the registration key field of the beacon message, the NIM is permitted to send a single discovery reply message to the RDS if such a reply is warranted. If the modulo of the NIM's IP address does not match the registration key field of the beacon message, the NIM remains silent and waits for the next beacon before responding. In a typically preferred embodiment, the value stored in the registration mod field of the beacon message is never less than two, and the value stored in the registration key field is always less than the value stored in the registration mod field. Those skilled in the art will understand that it is not necessary to use the IP address as the basis of the computation; any value that is unique to the device can be used without departing from the scope of the intended invention.

Closed Endpoint List

In the event that network connectivity with a NIM is lost, the RDS may be programmed to end a communication session with the NIM by timing out the TCP/IP connection with the NIM. When this occurs, it abortively closes the TCP/IP connection and places a notification about the closure in the beacon message in the form of the IP address and port number of the TCP/IP connection that was closed. In one embodiment of the present invention, there are five separate fields: three fixed-size fields and two variable length fields, that comprise the closure notification, which is hereinafter referred to as the closed endpoint data.

The first fixed length field of the closed endpoint data is the closed endpoint list start offset field. This field contains the offset (in bytes) within the beacon message at which the list of closed endpoints can be found. This offset is started from the very beginning of the beacon message.

The next fixed length field of the closed endpoint data is the closed endpoint list entry count field. This field contains the number of closed endpoints that are listed in the variable length IP address and port number fields at the end of the beacon message.

The third fixed length field of the closed endpoint data is the closed endpoint list entry lifetime field. This field contains the number of consecutive beacon messages in which each closed endpoint will be listed. For example, if this value is 5, and a TCP/IP connection is closed by the RDS, the closed endpoint data will be placed into the next available beacon message, and then repeated for the next 4 beacon messages. The value in the closed endpoint list entry lifetime field is never less than one.

As is depicted in FIG. 5, the actual data for the closed endpoints is stored in the variable-length fields at the end of the beacon message. Closed endpoint data consists of the IP address and port number of a TCP/IP connection that was closed. Because these values are 4 bytes and 2 bytes long, respectively, they can not be placed in the message together without causing alignment problems. To prevent wasting time and space padding the data to fit the field lengths, the IP addresses and port numbers are stored separately in their own lists. These lists are constructed such that the elements correspond with each other, that is, when stepping through each list, the first IP address is in sync with the first port, the second address with the second port, and so forth. This implies that the number of IP addresses and port numbers are always equal, although it is possible in some embodiments to have unequal IP addresses and port numbers, although suitable padding, or default spacing, must be provided.

Beacon Interval

Referring again to FIG. 5, the second variable length field of the closed endpoint list is the beacon interval field. This field contains a value that indicates how frequently the RDS is transmitting beacon message packets. Typically, this value is expressed in milliseconds, and the inventors have found that the program is most efficient if the value is equal to or greater than 1000 (one second), although the process functions acceptably if the value is less than 1000, although not as efficiently in terms of resource management and data flow.

Time

The three Timestamp fields shown in FIG. 5 contain the current time/date from the RDS. This information can be used, if desired, to synchronize the clock of a remote device with the clock of the RDS. Generally, in this embodiment of the present, timestamps are supplied in UTC time, to avoid problems with internationalization, daylight savings, and the like. However, if the entire system is running in accordance with a time standard other than UTC time, appropriate time standards may also be used as long as they are compatible with all devices on the network.

In one embodiment of the present invention, the first of the timestamp fields, the UTC time of year field, contains the number of hundredths of seconds that have elapsed since 12:00 a.m. on January 1 of the current year, and the second timestamp field, the UTC year field, contains the current UTC calendar year. The local time offset field, the third timestamp field, contains a signed value representing the difference, typically in minutes, between local time and UTC time.

Future Data

The section of the RDS message beacon depicted in FIG. 5 labeled "possible additional data (future revisions)" provides space in the beacon message for any future fixed-size fields that may be added to the beacon at a later time, thus allowing for enhancement or expansion of the beacon message. Providing for future changes to the message beacon in this manner is advantageous since the closed endpoint data fields are variable-length, and thus are best placed at the end of the message to make parsing of the beacon message and access to the other fixed-size fields easier to accomplish computationally. Typically, the software running on the NIM will expect extra data, and will ignore that data unless specifically programmed otherwise, such as in a revision of the software that is populated to all, or selected ones, of the NIMs on the network.

NIM Status Reply

In one preferred embodiment of the present invention, NIMs constantly listen on a selected UDP port for incoming messages, and the NIM checks every message that is received to see if it is a valid RDS beacon message. If the received message is a valid RDS beacon message, and if certain conditions, which will be discussed in more detail below, are met, the NIM responds to the RDS beacon by sending a NIM status reply message back to the UDP port on the RDS server from which the beacon message originated.

Figures 6, 12:
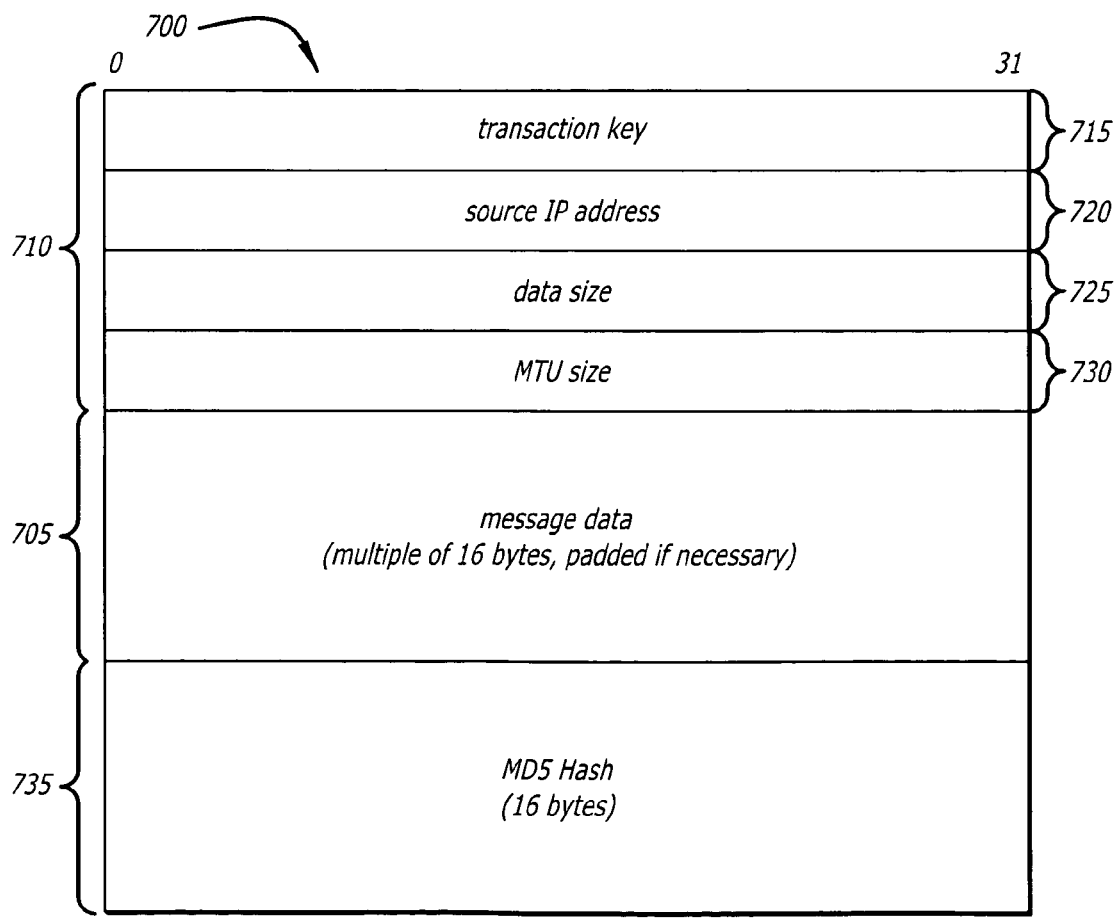
FIG. 6 is a diagram illustrating the data structure of a status reply message transmitted by a NIM in accordance with one embodiment of the present invention.
FIG. 12 is a diagram illustrating the format of a secure message encrypted in accordance with one embodiment of the present invention.

FIG. 6 illustrates the data format of one embodiment of the NIM status reply message. As with the beacon message, all data fields having a length greater than one byte are generally stored in little-endian format. In one embodiment, the total size of the NIM status reply message generally does not exceed 512 bytes, although it is possible to construct a valid status reply message larger than 512 bytes, and such messages are within the scope of the present invention. Also, like the RDS beacon message described above, an additional layer of encryption may be applied to the status reply message before it is transmitted to enhance security of the message. Each of the fields of the NIM status reply message are described in detail below.

Message ID

As shown in FIG. 6, the first byte of the status reply message is the message ID field. This byte is constant, and is used to identify the message as a NIM status reply message.

Connected/Listening Endpoint Lists

The next field of the embodiment of the status reply message depicted in FIG. 6 is the endpoint list start offset field. Generally, a NIM is programmed to allow for the possibility of providing connectivity to several client devices at once, such as, for example, via a USB hub. Every device attached to a NIM that is capable of processing application-level messages from the RDS is considered an endpoint, and is given its own dedicated TCP/IP connection to the RDS by the NIM. When the NIM sends a status reply message it includes a list of every available endpoint, in the form of a list of TCP/IP ports, to which the RDS can create connections. This list is divided into two subgroups: ports that currently have a valid connection to the RDS, and ports that are listening for a beacon so that a new connection to the RDS may be opened.

The endpoint list start offset field contains a value representing the offset in bytes within the status reply message at which the list of endpoint port numbers can be found, and the offset is started from the very beginning of the status reply message. The list of endpoint ports is simply an array of TCP/IP port numbers, with each entry being 2 bytes in length. In one embodiment, the first part of the list contains the port numbers for all of the connected endpoints, followed immediately by the port number for the listening endpoints.

The connected endpoint count field contains a value representing the number of endpoints that currently have a valid connection to the RDS The listening endpoint count field contains a value representing the number of endpoints that are listening for a new connection from the RDS. The value of either of these fields may be zero at any given time, and the sum of the connected endpoint count field and listening endpoint count field will typically never exceed 255, although longer fields may be used if the lengths of other indicators in the message are adjusted appropriately so that the message may be parsed and read by the RDS server.

Future Data

Like the RDS beacon message, the NIM status reply message provides for future expansion between the fixed-size and variable length data fields by providing an area in the message string that may be used in future versions. This area of the status reply message ensures that future implementations of the protocol of the present invention expect and ignore extra data in the message.

NIM Discovery Flow

Figure 7A:
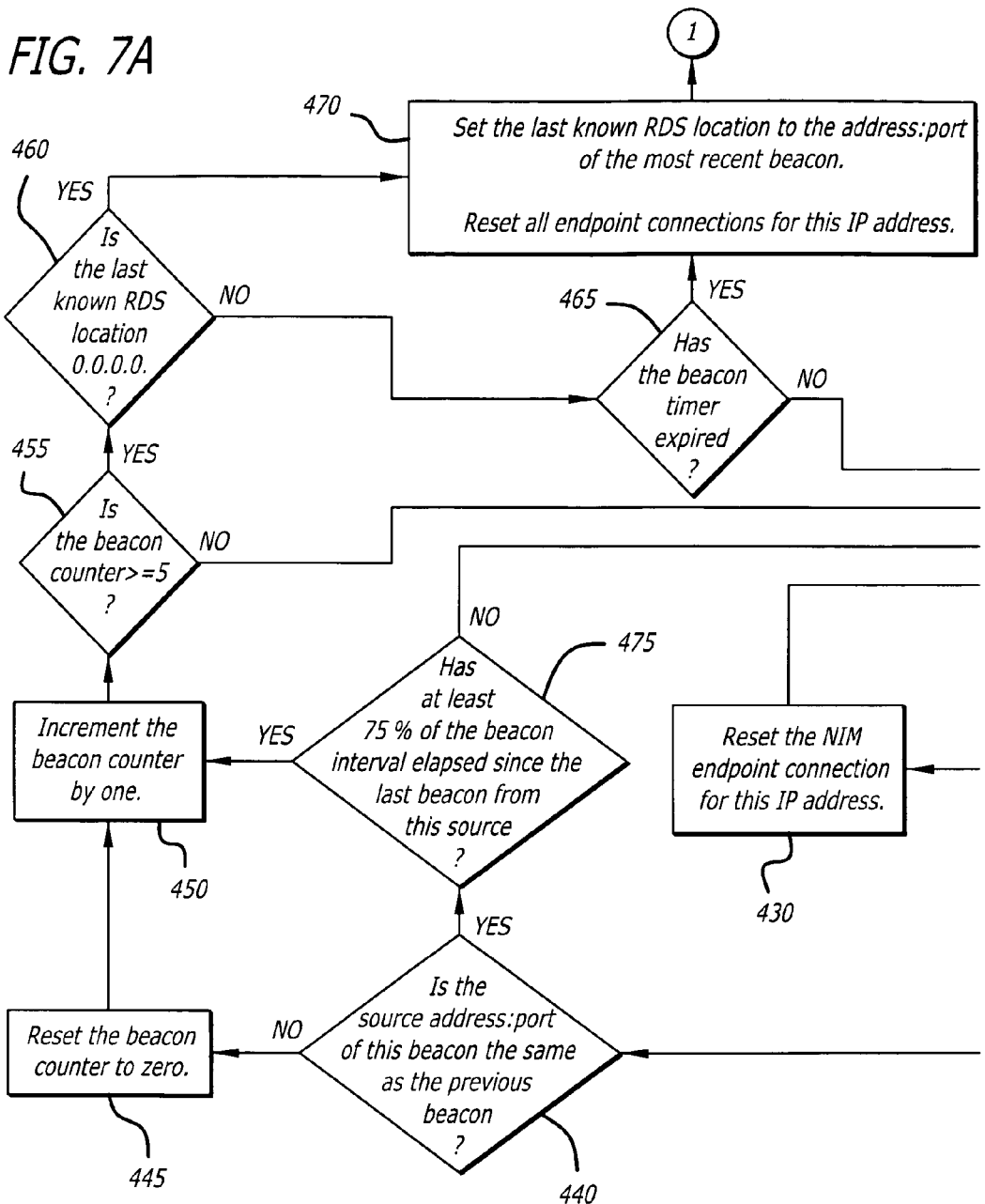
FIG. 7 is a flow chart depicting the logic flow of one embodiment of the discovery process of the present invention carried out by a NIM.
Figure 7B:
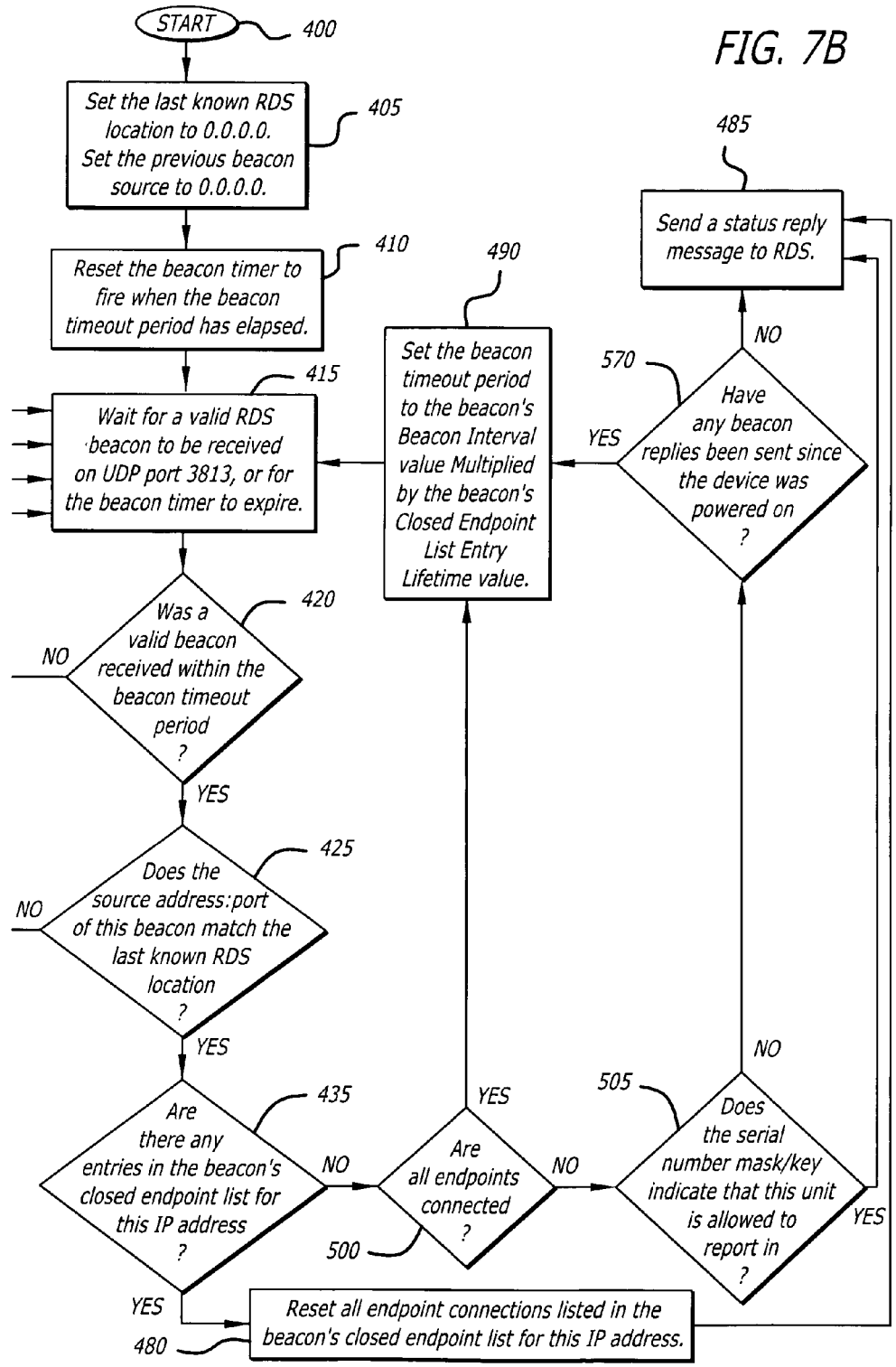

FIG. 7 is a flow chart showing, from the NIM's point of view in the system, the flow of one exemplary embodiment of the discovery method of the present invention. It is advantageous to view the discovery process from the NIM side of the connection, since the RDS's flow typically focuses primarily on managing an endpoint cache.

When a NIM starts up, it begins by listening for beacon messages on a selected port. In a preferred embodiment, the NIM is typically programmed to not attempt to reply to a beacon message until at least 5 consecutive valid beacon messages have been received from the same IP address and port number, with at least 75% of the beacon interval contained in the beacon message occurring between each beacon message. This condition is advantageous in enhancing security of the system in that it prevents the NIM from being fooled by a rogue system attempting to impersonate a RDS and gain control of the devices attached to the NIM. An additional advantage of this system is that if the NIM receives overlapping beacon messages, indicating an additional server, or subnet, that is trying to communicate with the NIM, the NIM will ignore the overlapping beacon message and will not register with any of the servers whose beacon messages have been received by the NIM.

Once the programmed logic of the NIM is confident that it has received a valid RDS beacon message, the NIM begins the registration process by parsing the beacon message and compiling a NIM status reply message. In many embodiments of the present invention, the NIM is programmed to check the registration mod and key fields in the beacon message to determine whether it is allowed to report itself to the RDS immediately. Checking to see if an immediate response is required, or if it is allowed to skip this beacon message and reply to a latter beacon message, is an optimization method designed to improve nominal discovery speed. As stated above, this optimization step is useful where network connectivity to a large number of NIMs has been lost and then restored, resulting in the possibility of flooding the RDS with registration requests.

When the NIM has determined that the RDS beacon message is valid, the NIM drops into a mode of constantly monitoring RDS beacon messages. Every beacon message that is received from the RDS is examined to see if any of the NIMs endpoints are listed in the beacons closed endpoint list. If so, it means that the TCP/IP connections for the listed endpoints have been timed out and closed by the RDS, and the NIM should do the same to make sure the RDS and NIM are in sync with each other. Whenever the NIM sees a beacon with one or more of its endpoints in the closed endpoint list, the NIM is required to send a status reply message after closing the requested connections. This is done without regard to the values of the registration mod and key fields.

If no endpoints are listed in the beacon message's closed endpoint list, the NIM looks at the registration mask and key fields to determine whether a window has arrived for reporting changes to the RDS. If not, the NIM simply waits for the next beacon message. If the NIM's window has arrived, the NIM sends a status reply message to the RDS if any of the NIM's endpoints are unconnected and listening for a new TCP/IP connection.

Describing the process set forth in FIG. 7 in more detail, when the NIM starts up in box 400, the processor of the NIM sets the last known RDS location to an IP address of 0.0.0.0, and sets the previous beacon source to 0.0.0.0 in box 405. The NIM also sets the beacon counter to zero and sets the beacon timeout period to infinity in box 405. The NIM also resets the beacon time to fire when the beacon timeout period has elapsed in box 410.

The NIM, in box 415, then waits for a valid RDS beacon message to be received on, for example, UDP port 3613 (or some other selected port), or for the beacon timer to expire. In box 420, the operating programming of the NIM analyzes whether a valid beacon message was received within the beacon timeout period. If a valid beacon message was received, the process continues to box 425 where the NIM determines whether the source address and port number of the beacon message matches the last known RDS location. If a valid beacon message has not been received in box 420, the process branches to box 430 and the NIM resets the NIM endpoint connection for this IP address, and returns to box 415 and waits for a valid RDS beacon message to be received.

If a valid beacon message was received in box 420, and the source address and port number match the last known RDS location in box 425, the process branches to box 435 and the NIM determines whether there are any entries in the beacon message's close endpoint list for this IP location. If the source address and port number do not match in box 425, the process branches to box 440 and the NIM determines whether the source address and port number of the present beacon message are the same as the last previous beacon message received. If the source address and port number of the present beacon message are not the same as the last previous beacon message received, the process branches to box 445 and the NIM resets the beacon counter to zero, increments the beacon counter by one in box 450, determines if the beacon counter is greater than or equal to five in box 455, and if the beacon counter is not greater than or equal to five, the process branches back to box 415 and the NIM continues to wait for a valid RDS beacon message. If the beacon counter is determined to be greater than or equal to five in box 455, the process continues to box 460 and the NIM determines if the last known RDS location was 0.0.0.0. If the last known RDS location was not 0.0.0.0, the process branches to box 465 and the NIM determines if the beacon timer has expired. If the beacon timer has not expired, the process returns to box 415 and the NIM waits for a valid beacon message. If the beacon timer has expired in box 465, or if the last known RDS location is determined to be 0.0.0.0 in box 460, then the process branches to box 470 and the NIM sets the last known RDS location to the address and port number of the most recent beacon message, and resets all endpoint connections for this IP address.

As indicated in FIG. 7, the process then continues from box 470 to box 505 where the NIM determines if the serial number mask/key indicates that this unit is allowed to report in to the RDS. If the NIM determines that the serial number mask/key indicates that the NIM is allowed to report in to the RDS, then the process continues to box 485 and the NIM sends a status reply message to the RDS, continues to box 490 and sets the beacon timeout period to the beacon message's beacon interval value multiplied by the beacon message's closed endpoint list entry lifetime value, returns to box 410 and resets the beacon timer to fire when the beacon timeout period has elapsed, and continues to box 415 to wait for a valid RDS beacon message to be received.

If the NIM determines in box 505 that the serial number mask/key indicates that the unit is not allowed to report in to the RDS at this time, the process branches to box 510 and the NIM determines whether any beacon message status reply messages have been sent since the NIM was powered on. If status reply messages have been sent since the NIM was powered on, the process continues to box 490 and the NIM sets the beacon timeout period to the beacon message's beacon interval value multiplied by the beacon message's closed endpoint list entry lifetime value, returns to box 410 and resets the beacon timer to fire when the beacon timeout period has elapsed, and continues to box 415 to wait for a valid RDS beacon message to be received. If the NIM determines, in box 510, that no status reply messages have been sent, the process branches to box 485 and the NIM sends a status reply message to the RDS, continues to box 490 and sets the beacon timeout period to the beacon message's beacon interval value multiplied by the beacon message's closed endpoint list entry lifetime value, returns to box 410 and resets the beacon timer to fire when the beacon timeout period has elapsed, and continues to box 415 to wait for a valid RDS beacon message to be received.

If the source address and port number of the current beacon message is determined to be the same as the previous beacon in box 440, the process continues to box 475 and the NIM determines if at least 75 percent of the beacon interval has elapsed since the last beacon message from the same source. If at least 75 percent of the beacon interval has not elapsed since the last beacon message from the same source, the process returns to box 415 and the NIM waits for a valid RDS message beacon.

If at least 75 percent of the beacon interval has elapsed since the last beacon from the same source, the process continues to box 450 and the NIM increments the beacon counter by one, determines if the beacon counter is greater than or equal to five in box 455, and if the beacon counter is not greater than or equal to five, the process branches back to box 415 and the NIM continues to wait for a valid RDS beacon message. If the beacon counter is determined to be greater than or equal to five in box 455, the process continues to box 460 and the NIM determines if the last known RDS location was 0.0.0.0. If the last known RDS location was not 0.0.0.0, the process branches to box 465 and the NIM determines if the beacon timer has expired. If the beacon timer has not expired, the process returns to box 415 and the NIM waits for a valid beacon message. If the beacon timer has expired in box 465, or if the last known RDS location is determined to be 0.0.0.0 in box 460, then the process branches to box 470 and the NIM sets the last known RDS location to the address and port number of the most recent beacon message, and resets all endpoint connections for this IP address.

In the case where the source address and port number of the current beacon is determined in box 425 to match the last known RDS location, the process continues to box 435 and the NIM determines if there are any entries in the beacon message's closed endpoint list for this IP location, and if so, resets all endpoint connections listed in the beacon message's closed endpoint list for this IP address in box 480, sends a status reply message to the RDS in box 485, sets the beacon timeout period to the beacon message's beacon interval value multiplied by the beacon message's closed endpoint list entry lifetime value in box 490, returns to box 410 and resets the beacon timer to fire when the beacon timeout period has elapsed, and continues to box 415 to wait for a valid RDS beacon message to be received.

If the process determines in box 435 that there are no entries in the beacon message's closed endpoint list for this IP address, the process branches to box 500 and the NIM determines whether all endpoints are connected. If all endpoints are connected, then the process continues to box 490 and the NIM sets the beacon timeout period to the beacon message's beacon interval value multiplied by the beacon message's closed endpoint list entry lifetime value, returns to box 410 and resets the beacon timer to fire when the beacon timeout period has elapsed, and continues to box 415 to wait for a valid RDS beacon message to be received.

If all endpoints are determined in box 500 to not be connected, the process branches to box 505 where the NIM determines if the serial number mask/key indicates that this unit is allowed to report in to the RDS. If the NIM determines that the serial number mask/key indicates that the NIM is allowed to report in to the RDS, then the process continues to box 485 and the NIM sends a status reply message to the RDS, continues to box 490 and sets the beacon timeout period to the beacon message's beacon interval value multiplied by the beacon message's closed endpoint list entry lifetime value, returns to box 410 and resets the beacon timer to fire when the beacon timeout period has elapsed, and continues to box 415 to wait for a valid RDS beacon message to be received.

If the NIM determines in box 505 that the serial number mask/key indicates that the unit is not allowed to report in to the RDS at this time, the process branches to box 510 and the NIM determines whether any beacon message status reply messages have been sent since the NIM was powered on. If status reply messages have been sent since the NIM was powered on, the process continues to box 490 and the NIM sets the beacon timeout period to the beacon message's beacon interval value multiplied by the beacon message's closed endpoint list entry lifetime value, returns to box 410 and resets the beacon timer to fire when the beacon timeout period has elapsed, and continues to box 415 to wait for a valid RDS beacon message to be received. If the NIM determines, in box 510, that no status reply messages have been sent, the process branches to box 485 and the NIM sends a status reply message to the RDS, continues to box 490 and sets the beacon timeout period to the beacon message's beacon interval value multiplied by the beacon message's closed endpoint list entry lifetime value, returns to box 410 and resets the beacon timer to fire when the beacon timeout period has elapsed, and continues to box 415 to wait for a valid RDS beacon message to be received.

It is expected that a beacon packet will be lost from time to time, due to the unreliable nature of UDP message system. Generally, lost packets are not a problem unless a large number of consecutive packets are lost, as this indicates an extended loss of connectivity with the RDS. Each RDS beacon packet contains a closed endpoint list entry lifetime field which indicates the total number of consecutive beacon messages in which the RDS will post endpoint closure information for a given endpoint. If no beacons messages are received for an amount of time long enough for the number of indicated beacon messages to be transmitted by the RDS, the NIM typically assumes that one or more of its connections may have been closed by the RDS. When this happens, the NIM is programmed to deliberately drop one of its connections, causing it to report in to the RDS during its next reply window. This gives the RDS a chance to re-post any closed endpoints in the beacon message, so the RDS and NIM may sync up again.

If the NIM starts seeing RDS beacon messages from a second source at any time after it has already registered with a particular RDS, the NIM ignores the second source's beacon messages in favor of messages from the RDS it is registered with. If, however, the original RDS server stops transmitting beacon messages for some reason, and a predetermined number of consecutive beacon messages, such as, for example, five, are received from a new RDS server, the NIM resets all of its endpoint connections and registers with the new server. This is advantages as it allows the NIM to switch servers in the event that a primary RDS server goes down and a backup RDS server is brought online to take its place. It will be understood by those skilled in the art that, while this embodiment of the present invention is described with reference to five consecutive beacon messages, the number of beacon messages may differ, according to the needs network or the desire of the system designer, and more or less than five beacon messages may be received before switching to the new server without departing from the scope of the present invention.

Figure 8:
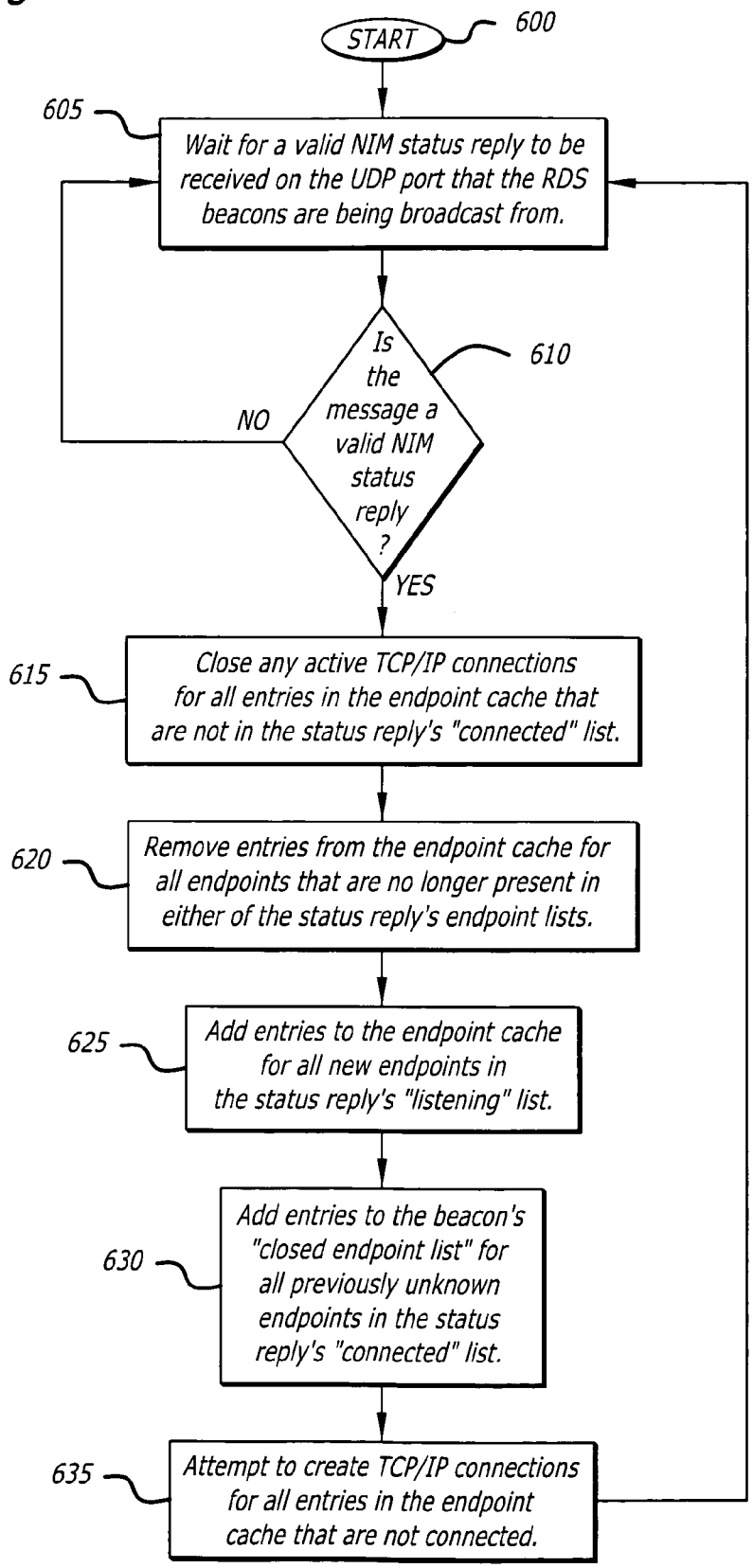
FIG. 8 is a flow chart depicting the logic flow of one embodiment of the RDS discovery process carried out by an RDS in accordance with one embodiment of the present invention.

FIG. 8 is a block diagram illustrating the RDS discovery program flow. As stated earlier, the RDS discovery flow is mainly concerned with watching for replies to its beacon messages and managing its endpoint cache using the data received in the status reply messages it receives from NIMS connected to the network.

After starting up in box 600, in box 605 the RDS waits for a valid NIM status reply message to be received on the UDP port that the RDS beacon messages are being broadcast from. If a message is received on the UDP port, the process continues to box 610 and the RDS's programming logic determines if the message is a valid NIM status reply message. If the message is not a valid NIM status reply message, the process returns to box 605 and the RDS continues to wait for a valid status reply message.

If the message is a valid status reply message, the process continues to box 615 and the RDS closes any active TCP/IP connections for all entries in the endpoint cache that are not in the status reply message's "connected" list. Once this is accomplished, the process continues to box 620 and the RDS removes entries from the endpoint cache for all endpoints that are no longer present in either of the status reply messages endpoint lists. Once this activity is completed, the process continues to box 625 and adds entries to the endpoint cache for all new endpoints in the status reply message's "listening" list, and then continues to box 630 and adds entries to the beacon message's "closed endpoint list" for all previously unknown endpoints in the status reply message's "connected" list.

After adding entries to the beacon's "closed endpoint list" for all previously unknown endpoints in the status reply's "connected" list, the process continues to box 635 and the RDS attempts to create TCP/IP connections for all entries in the endpoint cache that are not connected. When the process of box 635 is complete, the RDS returns to box 605 and waits for a valid NIM status reply message to be received.

Resetting Connections

Whenever a TCP/IP connection is timed out, an abortive close is performed on the connection. If, the interruption in connectivity is not much longer than the timeout period, then it is possible, but not guaranteed, that the system on the other end of the connection will be notified of the closure. To be safe, however, it must be assumed that the interruption in connectivity will last for an extended length of time, and that such notification will not occur. Accordingly, after the connection has been closed, the system and method in accordance with the present invention performs several processes to ensure that the two endpoints can get back in sync. The processes are different for the RDS compared to a NIM, and are described more fully below.

The process for the NIM is somewhat simpler than the process used by the RDS. Whenever the NIM resets a connection, it simply waits for an opportunity to send a status reply message, after checking the registration key in the RDS beacon message, and sends a status reply message indicating that the recently closed endpoint port is now in a listening mode. When the RDS sees this, it resets its connection to the endpoint and creates a new TCP/IP connection. The NIM continues to report the unconnected endpoint, when allowed, until the RDS finally creates a new TCP/IP connection to the port.

If the RDS drops the connection, it must put the endpoint's address and port number in the beacon message's closed endpoint list. Closed endpoint information is published in the list for a number of beacon messages equal to the closed endpoint list entry lifetime value. The RDS then assumes that, at some point, the NIM will send a status reply message indicating that the endpoint is once again in a listening mode, and waits to receive such a status reply message from the NIM.

If the NIM misses all of the beacon messages, the NIM's programming logic will flag itself as needing to report to the RDS as soon as connectivity is restored. When the NIM does finally report to the RDS by sending a status reply message to the RDS, if the closed endpoint is still listed as connected, the RDS once again puts the endpoint into the beacon message's closed endpoint list, and waits for the NIM to reply stating that the port is in a listening mode.

Connection Management

Once the NIMs connected to the network have registered with the RDS, the RDS creates TCP/IP connections to each endpoint on every NIM. This provides a reliable means of delivering large application-level messages between the RDS and the endpoints. This is also advantageous in that only the RDS can create a connection to the NIM, and the NIM is programmed to ignore any messages not originating with an RDS. Moreover, the NIM will respond to messages only from the RDS to which it is registered, and will ignore messages from other servers, including rogue servers attempting to impersonate a valid RDS server.

By default, the TCP/IP protocol attempts to resend data on a connected socket for up to nine minutes before the TCP/IP connection is programmed to give up and declare the connection broken. In addition, the TCP/IP protocol only provides negative confirmation of data delivery; that is, it only notifies the sender when the data could not be sent, not when the data has been successfully sent. Because the RDS requires a much shorter timeout than this, and requires positive confirmation of message delivery, extra handshaking is typically performed across the TCP/IP connections when sending application messages.

Message Flow

Only one application-level message at a time is ever sent in a given direction across a TCP/IP connection. This serialization simplifies control of the data flow considerably, since the system may perform what amounts to an application-level timeout on the TCP/IP connection. If some kind of queuing interface is desired, it is typically implemented in the application layer.

Figure 9:
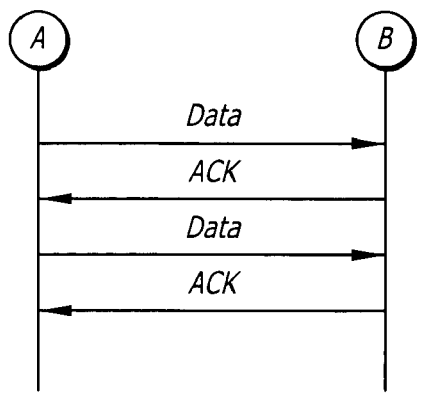
FIGS. 9-11 depict the flow of requests and acknowledgments within a TCP connection.
Figure 10:
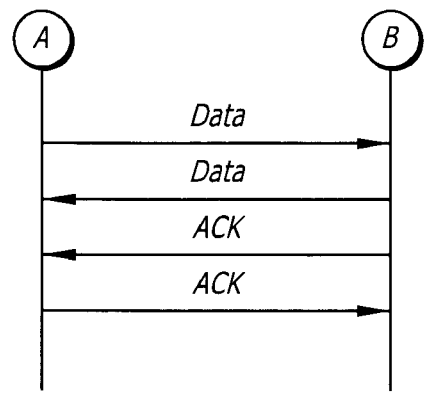

FIG. 9 illustrates an example of the message flow between two endpoints, identified as A and B. After sending data, the sender must wait until it receives an ACK, typically a message zero bytes in length, from the receiver before it can send another data message. Since the connection is bi-directional, this flow can occur in both directions at once, as depicted in FIG. 10.

Figure 11:
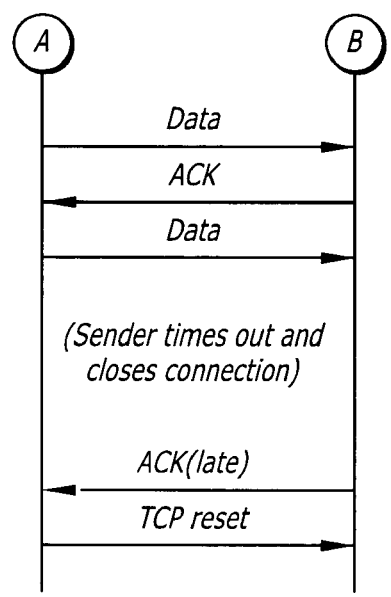

FIG. 11 depicts an exemplary data flow across a TCP/IP connection where the sender, in this example, A, performs an application level timeout. Because the ACK for the second data message did not arrive within the timeout period, endpoint A forcibly closed the TCP connection between the devices. If or when the ACK from endpoint B finally does arrive at sender A, the TCP stack replies with a low-level connection reset error indicating that the connection has been closed. Any further messages sent by endpoint B receive the same error.

Data Encryption

In order to protect sensitive patient data, as well as harden the overall system against malicious attacks, one embodiment of the connectivity protocol of the present invention performs encryption on all data that is sent across the network. In the embodiment of the present invention described, encryption is a four-step process, with each step designed to address different security concerns.

FIG. 12 illustrates the structure of an encrypted message 700 of one embodiment of the present invention. The particular embodiment of data encryption scheme illustrated does not support streamed data, and all messages sent between a NIM and RDS must be of a predetermined length. While this embodiment is described with reference to a predetermined length, other embodiments of the present invention contemplate the use of encryption schemes that are capable of encrypting messages having differing lengths, and are within the intended scope of the present invention.

Encryption Process

The first step in the encryption process of the illustrated embodiment is to pad the data to be transmitted to a multiple of 16 bytes. This is necessary because the final encryption step uses a symmetric block cipher with a fixed block size of 16 bytes. The pad data must be explicitly set to some constant or random values, and the message buffer's pre-existing memory contents may not be allowed to remain intact in the padded region. The padded data is stored in the message data field 705 of message 700.

A security header 710 comprising four fields 715, 720, 725 and 730 is then prepended to each message 700 as shown in FIG. 12. The transaction key field 715 of security header 710 contains a randomly generated 32-bit value which is generated by the most cryptographically strong random number generator available in the system. The source IP address field 720 of the security header 710 contains the sender's IP address, which is used by the receiver as a digital signature to authenticate the sender. The data size field 725 of the security header 710 contains the number of bytes in the original plaintext message, before padding. Finally, the MTU size field 730 of the security header 710 contains the maximum number of bytes that the sender can process in a single datagram, which, in this embodiment, is never less than 16 bytes.

After the security header 710 is prepended to the beginning of the message 700, a security footer 735 is appended to the end of the message 700. The security footer 735 in the illustrated embodiment contains a hash of the security header and padded message data, generated using, for example, the MD5 message digest algorithm. This security footer 735 is used by the receiver of the message to determine whether the message was tampered with during transit.

Once the entire message has been assembled, the transaction key in the security header is XORed with the entire message, 32 bytes at a time, excluding the transaction key itself. The "salting" of the data helps ensure that static portions of consecutive messages, such as the source IP address, do not get encrypted the same way each time, further strengthening the security of the encryption method of this embodiment of the present invention.

After the data has been salted, the entire message, including both headers, is encrypted with a shared key using, for example, the AES block cipher. The encrypted message is then sent to the intended recipient.

Decryption Process

Once the message is received, the programming logic of the receiver must first determine whether a valid message was received. This process varies slightly depending on whether the message is received on a datagram-based UDP or stream-based TCP connection.

In general, decryption is simply the reverse of the encryption process. In one embodiment of the present invention, the message is decrypted using the AES block cipher, then unsalted using the transaction key found in the security header. Once this is accomplished, the security header and padded data are hashed using the MD5 message digest algorithm, and the result is compared against the hash stored in the security footer. If the hashes match, the source IP address in the security header is checked against the actual source of the message. The data size field in the security header is then checked to make sure it is equal to, or at most 15 bytes less than, the actual size of the padded message data. If these final two checks pass, the data is considered to be valid, and can be extracted from the message for further use.

On TCP connections, the encrypted message may be delivered slowly, a few bytes at a time, over a period of time. This in itself is not a disadvantage, except that TCP connections have no concept of a beginning or end of a message. Therefore, the receiver takes an active role in determining the boundaries between consecutive messages sent over a TCP connection. As a result, the decryption process changes slightly when used over a TCP connection.

When decrypting a message received over a TCP connection using the methods of the illustrated embodiment of the present invention, the first 16 bytes are decrypted using the AES block cipher, unsalted using the transaction key, and examined to see if they contain a valid security header. If the source IP addresses match, and the data size is within a predetermined limit, the system continues to wait for additional bytes to be received until a message of the size specified in the security header has been received. If either of the values are invalid, however, the connection is dropped.

Once the required number of bytes have been received for a message of the specified size, the rest of the message is decrypted and unsalted, and the MD5 hash is verified. If the verification is successful, the data is considered to be valid; if the hash verification fails, the connection is dropped.

Transaction IDs in Reply Messages

In accordance with the principles of the present invention, the only data sent over UDP connections is the RDS beacon message and the NIM status reply message. Furthermore, the status reply message is only sent as a reply to the beacon message, and only one status reply message is sent per beacon message. Likewise, TCP connections only send messages, and ACK responses to those messages. In no case, however, are multiple replies sent (e.g. multiple beacon replies or multiple ACKs). Because of this, all message exchanges utilizing the principles of the present invention may be generalized to say that there is a 1:1 request/reply message ratio.

While the transaction ID in a message's security header has only been presented as a salt value to enhance the encryption process, this is not its only function. The transaction ID also provides synchronization between messages on both UDP and TCP connections.

Every request sent includes a randomly chosen transaction ID. Reply messages, however, do not choose their own transaction ID. Instead, they reuse the transaction ID from the request message, and set their own transaction ID field to zero. When the original requester receives a reply with a transaction ID of zero, it knows to use the transaction ID from the most recent request it sent to try and unsalt the data. As a result, the data will only decode correctly if the transaction IDs match.

Although no new messages are sent on a TCP connection until the zero-byte ACK is received, this method is advantageous in that it provides an extra degree of certainty. Even if the data size in the encrypted message is zero, the security header/footer must still decode properly and be valid, or else the connection is dropped. This provides 100% certainty than a given ACK reply is intended for a given request.

The methods of the present invention are even more advantageous when UDP connections are used, as those methods also provide protection against sequencing errors that might arise from out-of-order datagram delivery. Since the RDS chooses a new transaction ID for each beacon message, the transaction ID provides a means to verify whether a particular status reply message is a reply to the most recent beacon message, or whether it is an old reply that got delayed by the network.

MTU Discovery

The security header 710 (FIG. 12) at the beginning of every encrypted message contains an MTU size field 730 which indicates the maximum number of bytes that the system can process in a single datagram. This field is always set in every message, including ACK messages. A system can therefore safely discover the MTU size of another system by sending a zero-byte datagram, and examining the MTU size field of the ACK message. While this procedure is optional, it is advantageous since the receiver rejects any messages it receives that are larger than its MTU size.

AES Cipher Modes

The AES block cipher can be used in both electronic cookbook (ECB) and cipher block chaining (CBC) modes. CBC mode is slightly more secure, since it uses data from the previously encrypted block to salt the next block's data before encrypting. Using such a mode means that in order to decrypt an encrypted stream, a copy of the entire stream must be obtained, making it difficult to target specific excerpts.

According to the principles of the present invention, all TCP connections use CBC mode for the AES cipher to improve security, although use of other modes is possible, and intended to be within the scope of the present invention. Use of the CBC mode is not disadvantageous, since both ends of the data stream are always opened and closed in sync with each other. The RDS beacon messages and NIM status reply messages to the beacon messages, however, are sent over a UDP channel, and are thus sent and received without any synchronization and a NIM may power on and start receiving beacon messages long after the RDS started sending them. For this reason, it is advantageous for UDP channels to use ECB mode, since there is no way for NIMs to "catch up" on previously broadcast beacon messages.

In another embodiment of the present invention, a medical device may include a NIM that is programmed to "wake up" periodically when the medical device is connected to the network, but is otherwise inactive or powered down. In this embodiment, the NIM wakes up and begins listening to the network for beacon messages, as described above. This embodiment is advantageous because it allows the NIM to connect to the network so that it can receive updates to various databases that may be present in the memory of the medical device, or a storage media associated with the medical device, which may shorten the amount of time necessary for the medical device to boot up upon powering on. After any necessary updates have been received, the NIM is programmed to power down and return to "sleep" mode. The NIM may also power down after a specified period of time elapses without the receipt of any data, indicating that no updates to the database or databases of the medical device or associated equipment is necessary. In another embodiment, the NIM may be programmed to wake up independently of the medical device and store any data updates in a cache or other memory until the medical device is powered up, wherein the data will be provided to the medical device. This embodiment is advantageous in that is provides for conservation of battery power and prolongs battery life by only powering the NIM.

In yet another embodiment, the present invention provides a system and method for locating assets such as medical devices, which may be, for example, infusion pumps or vital signs monitoring equipment, that are typically moved from one location of an institution to another location in the course of patient treatment. This embodiment is particularly advantageous in institutions having mobile medical devices that communicate with the institutions network using wireless connections. In such a network, the mobile medical devices communicate with the network through transmitter/receivers located throughout the institution. Each transmitter/receiver is identified on the network with a MAC address. The location of each transmitter/receiver, and thus the location of each MAC address, is known to the system. Thus, care-givers wishing to locate mobile medical devices can be provided with a list of devices and the MAC addresses they are connected to, allowing the care-giver to determine the approximate location of the device, at least to the extent that the device is located within the range of the wireless transmitter/receiver. Typically, the range of such receivers in a medical institution is on the order of approximately sixty feet.

In still another embodiment, the present invention provides a system and method of locating mobile medical devices by establishing a watch list for devices that are known to exist within the institution, but which have not responded to a beacon message for a pre-determined period of time. In this embodiment, the system may be programmed to flag the device when the device is turned on or comes within range of a wireless transmitter/receiver, and thus begins responding to beacon messages transmitted by the RDS. A report that the flagged medical device has been located may then be provided to the institution.

While the specification describes particular embodiments of the present invention, those of ordinary skill can devise variations of the present invention without departing from the inventive concept.

We claim:

1. A method for discovering whether a client device connected to a number of endpoints is in communication with a server over a network, comprising:

broadcasting a beacon signal from the server from a selected port over the network;

listening on the selected port for a response signal generated by the client device communicated over the network in response to the beacon signal;

updating, based on the response signal, a list of endpoints in active communication with the server;

closing, based on the response signal, a communication session with an endpoint previously in communication with the server; and broadcasting, in a subsequent beacon signal, identities of any endpoints with whom the server has terminated a communication session.

2. The method of claim 1, wherein broadcasting the beacon signal further includes encrypting a message contained in the beacon signal.

3. The method of claim 1, further comprising:
receiving the beacon signal broadcast over the network;
determining whether a valid beacon signal was received; and
sending a response to a valid beacon signal over the network to register the client device with the server.

4. The method of claim 1, further comprising:
establishing a secure communications link between the server and the client device;
determining if the secure communications link has been closed;
resetting a list of connections maintained by the client device;
listening for a valid beacon signal; and
re-establishing the secure communications link.

5. A system for managing patient care in an institution, comprising:
a network for carrying data between devices connected to the network;
a server in communication with the network, the server having a processor programmed to broadcast a beacon signal over the network at a selected interval through a selected port of the server;
a network interface module (NIM) in communication with the network and programmed to listen to the network for the beacon signal from the selected port and respond to the beacon signal with a status message, the status message including information for use by the server in establishing a secure communication session with the NIM; and
a plurality of endpoints in communication with the server via the NIM, wherein an endpoint is a medical device;
wherein the beacon signal includes a list of endpoints for whom the server has ended a communication session;
wherein the status message includes a list of endpoints connected to the NIM with whom the server can create a communication session; and
wherein upon receiving the status message, the server uses the information contained in the status message to establish a communication session with an endpoint in the list of endpoints included in the status message.

6. The system of claim 5, wherein the NIM is also programmed to determine if the beacon signal is valid and to respond to the beacon signal only if the beacon signal is valid.

7. The system of claim 5, wherein the NIM and the server are communicate with the network through a wireless connection.

* * * * *